United States Patent
Sandstrom et al.

[11] Patent Number: 6,010,526
[45] Date of Patent: Jan. 4, 2000

[54] EPICARDIAL LEAD IMPLANT TOOL AND METHOD OF USE

[75] Inventors: Richard D. Sandstrom, Scandia; Keith A. Ufford, Chisago City, both of Minn.

[73] Assignee: Medtronic, Inc., Minneapolis, Minn.

[21] Appl. No.: 09/156,907

[22] Filed: Sep. 18, 1998

[51] Int. Cl.[7] .................................................... A61N 1/02
[52] U.S. Cl. ..................................................................... 607/1
[58] Field of Search .............................. 607/1; 600/377, 600/386, 434

[56] References Cited

U.S. PATENT DOCUMENTS

| | | |
|---|---|---|
| 3,737,579 | 6/1973 | Bolduc . |
| 4,066,085 | 1/1978 | Hess . |
| 4,207,903 | 6/1980 | O'Neill . |
| 4,271,846 | 6/1981 | Little . |
| 4,299,239 | 11/1981 | Weiss et al. . |
| 5,143,090 | 9/1992 | Dutcher et al. . |

*Primary Examiner*—Scott M. Getzow
*Attorney, Agent, or Firm*—Reed A. Duthler; Harold R. Patton

[57] ABSTRACT

A tool for implanting a pacing lead of the type having a fixation helix. The tool is provided a curved, elongated shaft with rotatable tongs mounted at its distal end. The tongs extend distally from the shaft and angle radially outward and slide against a bearing located in a distal portion of the shaft. A cable, rotatable and longitudinally movable relative to the shaft, extends through the shaft and is coupled to the tongs. A handle is mounted at a proximal end of the shaft and includes a mechanism for rotating the cable mechanism relative to the shaft and for moving the cable longitudinally relative to the shaft, so that the tons may grip rotate and release the tongs.

15 Claims, 4 Drawing Sheets

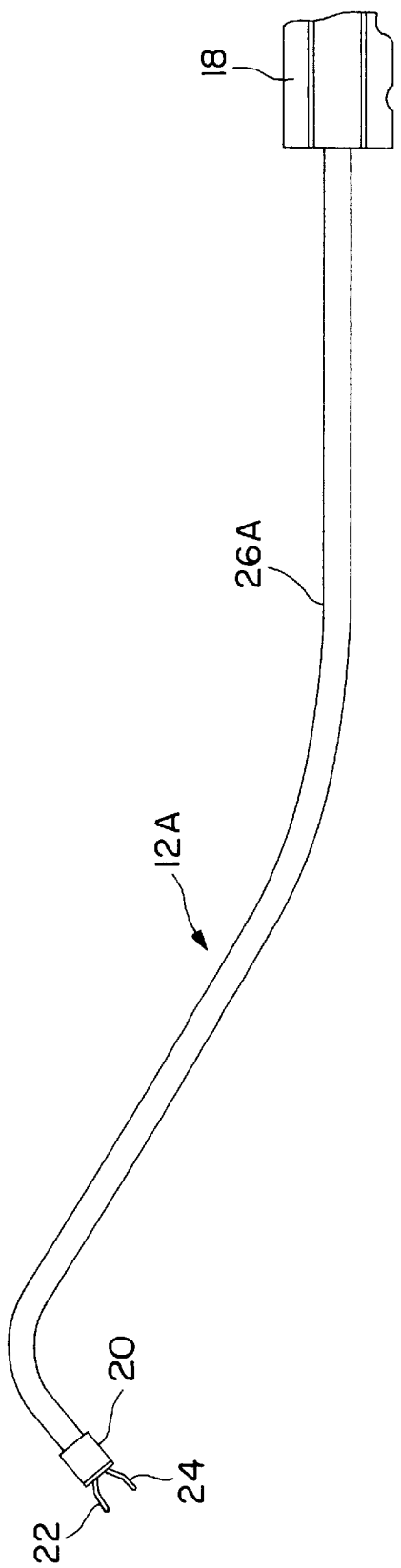
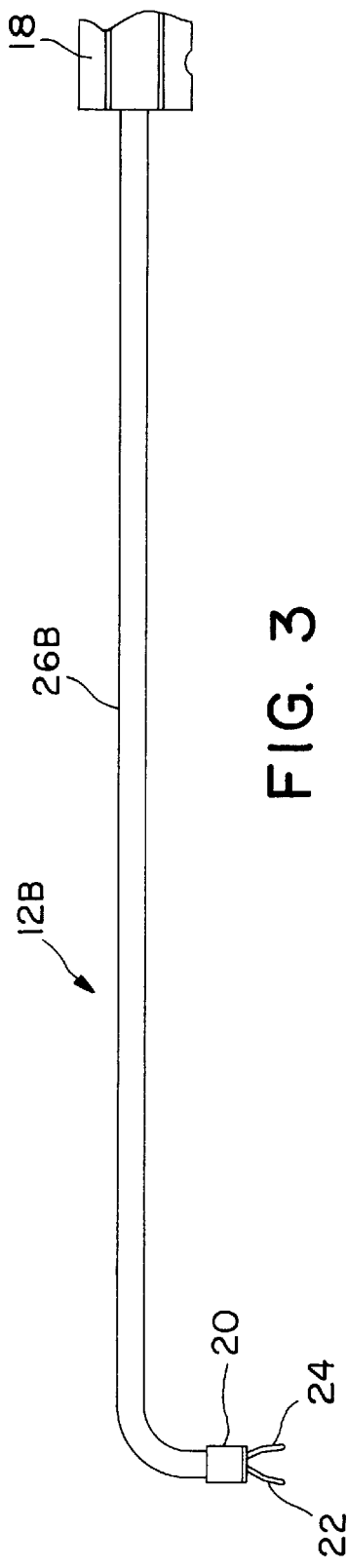
FIG. 2
FIG. 3

EPICARDIAL LEAD IMPLANT TOOL AND METHOD OF USE

BACKGROUND OF THE INVENTION

The present invention relates to implantable electrode leads generally and more particularly relates to tools for assisting in the implantation of electrode leads.

Implantable electrode leads employing helical fixation members which are screwed into body tissues have been employed for many years to pace the heart and to stimulate other locations within the body. Most typically the fixation helix also serves as the electrode. Examples of such leads include those described in U.S. Pat. No. 3,737,579 issued to Bolduc, U.S. Pat. No. 4,066,085 issued to Hess and U.S. Pat. No. 5,143,090 issued to Dutcher et al., both of which are incorporated herein by reference in their entireties. Typically, these leads are implanted using a tool which grips the lead adjacent its distal end and are be employed to twist or screw the fixation helix into body tissue. Typically, these tools have taken the form of elongated rods or shafts which have a mechanism at their distal end for gripping the lead adjacent the electrode. The tools may also have grooves or other mechanisms for locating the lead body, along their length. Such tools are disclosed in the above-cited Bolduc and Dutcher et al patents and in U.S. Pat. No. 4,299,239 issued to Weiss et al., U.S. Pat. No. 4,271,846 issued to Little and U.S. Pat. No. 4,207,903 issued to O'Neill. A disadvantage of these tools is that they are best suited for implanting electrodes in those circumstances in which the area to which the electrode is to be attached is readily accessible to the physician. For example, as discussed in the above cited patents, the tools may be used to attach lead to the anterior surface of the heart during a full or modified thoracotomy. These tools, unfortunately, are not as readily useful in conjunction with implanting leads in less readily accessible sites, such as the posterior surface of the heart.

SUMMARY OF THE INVENTION

The present invention is directed toward an implantation tool adapted for use in conjunction with electrode leads of the type employing helical fixation members and/or helical electrodes, which are intended to be screwed into body tissue. The present invention allows for placement of such leads in locations which are not readily accessible to the physician, such as the posterior surface of a human heart.

The lead insertion tool according to the present invention is provided with a handle and an elongated shaft which carries at its distal end a mechanism for gripping and releasing a distal portion of a screw-in lead, controllable using the handle portion of the tool. The elongated shaft portion of the tool is preferably curved so that it may be employed to reach around or beneath an organ, such as the heart, facilitating placement of the lead in more difficult to access locations such as the posterior surface of the heart. The gripping mechanism may be rotated relative to the shaft by means of a rotatable portion of the handle, allowing for the lead to be screwed into tissue, without movement of the shaft portion.

BRIEF DESCRIPTION OF THE DRAWINGS

FIG. 2 is a plan view of the shaft portion of a second embodiment of an implantation tool according to the present invention.

FIG. 3 is a plan view of the shaft portion of a third embodiment of an insertion tool according to the present invention.

DETAILED DESCRIPTION OF THE PREFERRED EMBODIMENTS

Figure 1:
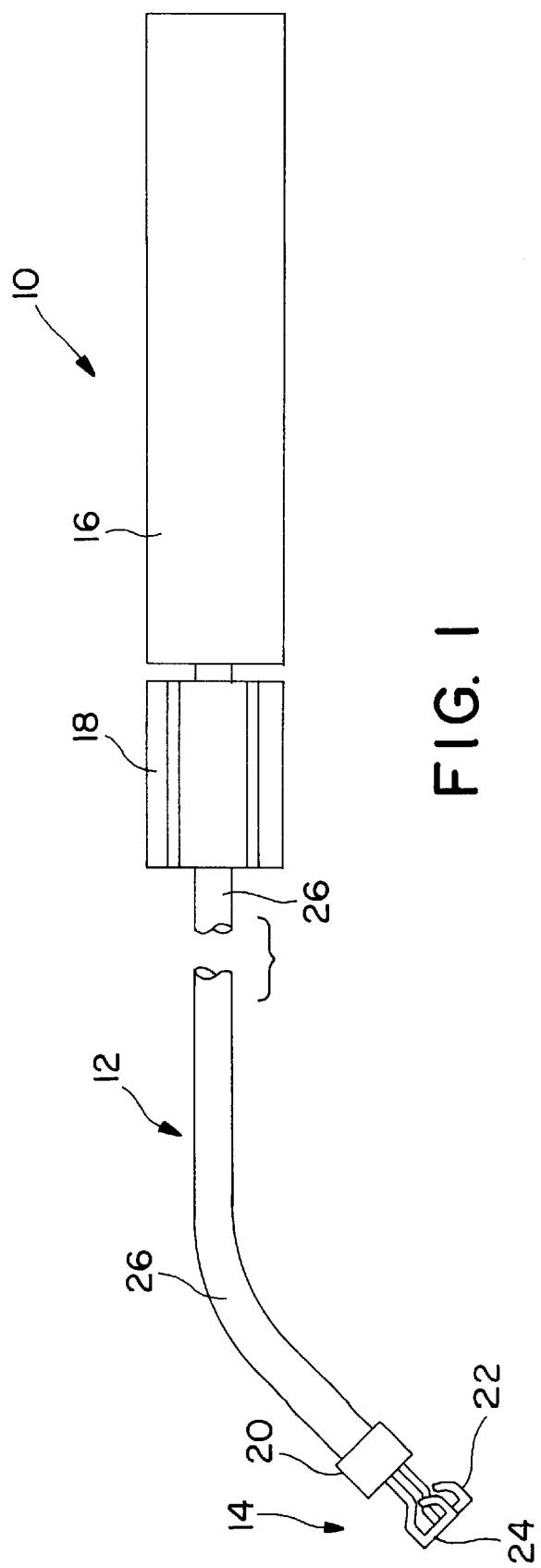
FIG. 1 is a plan view of an implantation tool according to the first embodiment of the invention.

FIG. 1 is a plan view of an implantation tool according to the present invention. At its proximal end is located a handle assembly 10 which includes a stationary or fixed handle portion 18 and a rotatable handle portion 16. Extending distally from the handle is the shaft portion 12 of the device, of which the outer shaft tubing 26 is visible. At the distal end of the shaft 12 is the gripping mechanism for releasably gripping the distal portion of an implantable lead having a screw-in type fixation mechanism. The attachment mechanism includes two metal tongs 22 and 24 which exit from nose piece 20, mounted to the distal end of outer shaft tubing 26. Stationary handle member 18 is fixedly mounted to outer shaft tubing 26.

Rotatable handle portion 16 is rotatable and longitudinally movable relative to shaft tubing 26 and stationary handle portion 18 and is coupled to metal tongs 22 and 24 by means of an internal drive cable, such that rotation of rotatable handle portion 16 relative to stationary handle portion 18 causes rotation of tongs 22 and 24 relative to outer shaft tubing 26 and nose cap 20. As will be discussed in more detail below, longitudinal movement of rotatable handle portion 16 relative to stationary handle portion 18 causes the tongs 22 and 24 to move closer or further from one another, facilitating gripping and releasing an implantable electrode lead. In this embodiment of the invention, the shaft tubing 26 is provided with approximately a 45° bend adjacent its distal end.

FIGS. 2 and 3 illustrate two alternative configurations for the shaft portion of an implantation tool according to the present invention. In FIG. 2, the shaft portion 12A includes outer shaft tubing 26A which is bent to form a sigmoidal curve as illustrated. In FIG. 3, the shaft 12B includes outer shaft tubing 26B which is curved to form an approximately 90° bend adjacent the distal end of tile shaft 12B. In both FIGS. 2 and 3, the stationary handle portion 18, tongs 22 and 24 and nose cap 20 correspond to those illustrated in FIG. 1.

Figure 4:
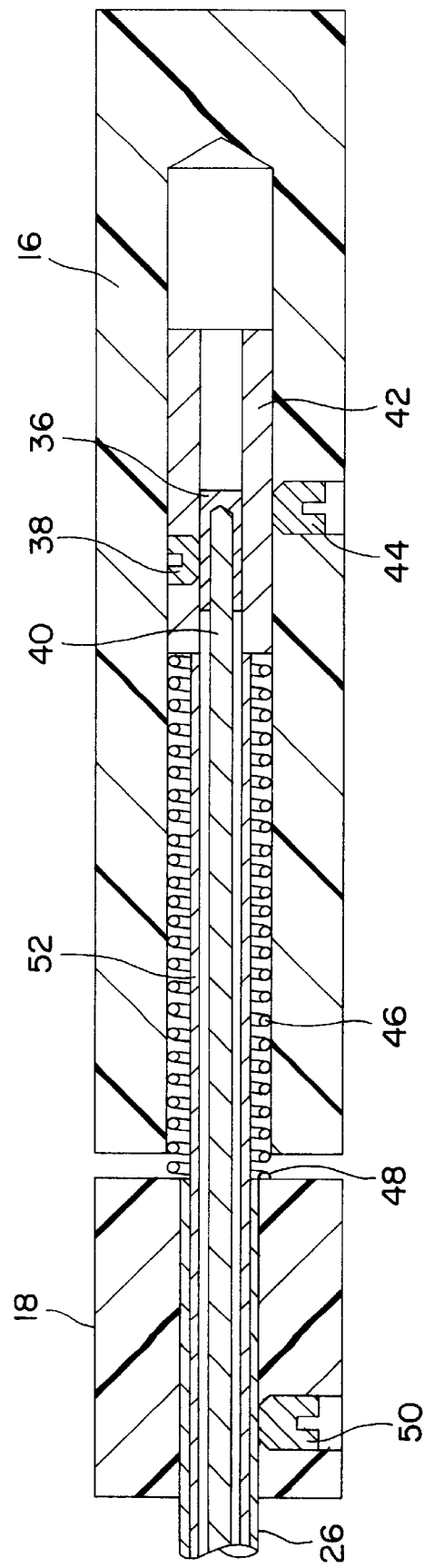
FIG. 4 is a sectional view through a handle of an insertion tool according to the present invention.

FIG. 4 is a sectional view through the handle of the implantation tool illustrated in FIG. 1. The proximal, rotatable portion of the handle 16 is provided with an internal lumen, in which a retainer block 42 is mounted. Retainer block 42 is maintained within the lumen of the rotatable handle portion 16 by means of a set screw 44. Within retainer block 42 is located a crimp sleeve 36 which is crimped to the proximal end of a cable 40, which is rotatable and longitudinally movable relative to the outer shaft tubing 26 and is coupled at its distal end to the tongs 22 and 24 (FIG. 1). The crimp sleeve 38 and cable 40 are fixedly retained within retainer block 42 by means of a second set screw 38. Rotation of rotatable handled portion 16 transfers torque to the tongs 22 and 24 (FIG. 1) via cable 40, causing the tongs to rotate along with the handle portion 16.

Also located within the rotatable handle portion 16 is a spring 46 which engages the distal end of the retainer block 42 and a plastic washer 48 located at the proximal end of stationary handle portion 18. Spring 46 maintains a force which tends to push the rotatable portion 16 of the handle proximally relative to the outer shaft tubing 26 and away from the stationary portion 18 of the handle, tending to withdraw the tongs 22 and 24 (FIG. 1) proximally into the nose cap 20 (FIG. 1). As discussed in more detail below, proximal movement of the tongs 24 and 22 into nose cap 20, sliding against bearing 30, causes them to move closer to one another, facilitating their gripping of an implantable electrode lead. By the same mechanism, movement of the rotatable handle portion 16 distally relative to the fixed handle portion 18 causes the tongs 22 and 24 to open, so that the electrode head may be inserted between the tongs. Allowing spring 46 to move the rotatable handle portion 16 proximally away from stationary handle portion 18 causes the tongs to move toward one another, gripping the lead. Spring 46, unless compressed by movement of the rotatable portion 16 of the handle, maintains the grip of the tongs 22 and 24 (FIG. 1) on the lead, so that the lead will remain gripped by the tong, until the physician deliberately chooses to release them by moving the rotatable handle portion 16 distally relative to the fixed handle portion 18.

The outer shaft tubing 26 extends within fixed handle portion 18 and is fixedly mounted thereto by means of a set screw 50. Inner shaft tubing 52 is located within the outer shaft tubing 26 and is fixed relative to retainer block 42 by crimping, and maintains the alignment of the rotatable handle portion 16 with the fixed handle portion 18. The inner shaft tubing 52 extends distally within the outer shaft to a point proximal to the curve adjacent the distal end of the outer shaft tubing 26. Outer shaft tubing 26, inner shaft tubing 52, spring 46, set screws 38, 44 and 50, sleeve 36, retainer block 42 and cable 40 are preferably fabricated of metal. Handle portions 16 and 18 and washer 48 are preferably fabricated of plastic or metal.

Figure 5:
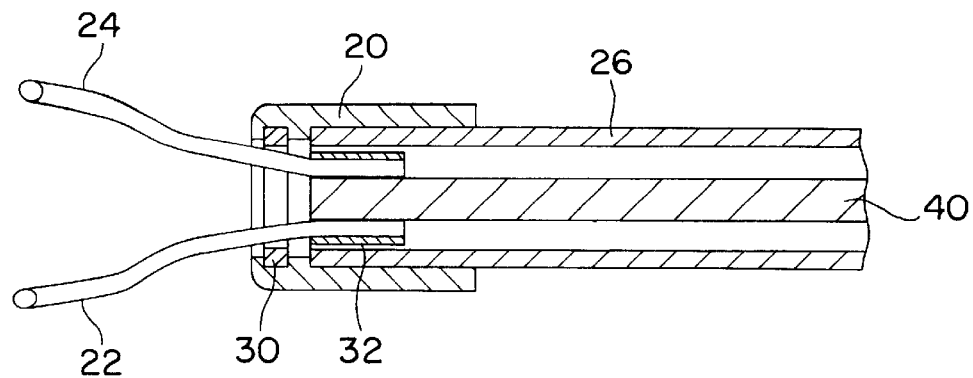
FIG. 5 is a sectional view through the distal portion of a shaft and associated attachment mechanism of an implantation tool according to the present invention.

FIG. 5 is a sectional view of the implant tool of FIG. 1 illustrating the distal portion of the outer shaft tubing 26 and the attachment mechanism in more detail. In this view, it can be seen that the nose piece 20 takes the form of a generally cylindrical member provided with a toroidal bearing 30 located internal to the distal opening of the cap member. The distal end of the cable 40 and the proximal ends of the tongs 22 and 24 are surrounded by a crimp sleeve 32 and are double crimped together. Rotation of cable 40 relative to head member 20 and outer shaft tubing 26 correspondingly causes rotation of tongs 22 and 24. The tongs angle outward from the crimping sleeve 32 and in a relaxed condition extend further radially outward than the inner surface of bearing 30. Proximal movement of cable 40 relative to the outer shaft tubing 26 and nose cap 20 causes the distal ends of the tongs 22 and 20 to move closer to one another, as the proximal portions of the tongs are forced closer to one another by sliding against bearing 30. Rotation of cable 40 causes rotation of the tongs 22 and 24 and the lead gripped by the tongs. Sleeve 32, tongs 24 and bearing 30 are preferably fabricated of metal. Nose cap 30 is preferably fabricated of plastic or metal.

Figure 6:
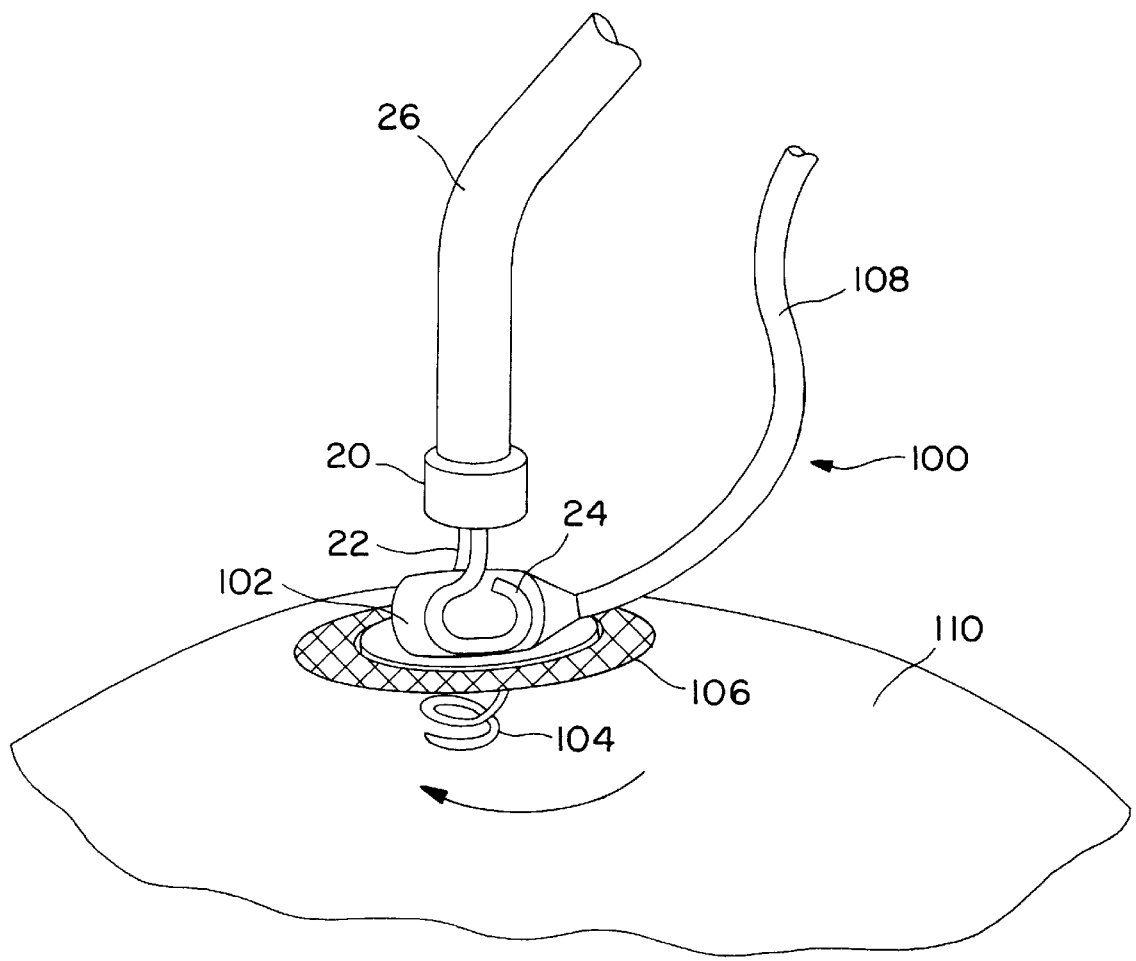
FIG. 6 is a perspective view of the distal portion of a shaft of an implantation tool according to the present invention, in which the attachment mechanism has engaged a screw-in type electrode, illustrating the use of the tool to attach the lead to the surface of a human heart.

FIG. 6 is a perspective view of the distal portion of the shaft 12 of the implantation tool illustrated in FIG. 1, in conjunction with a myocardial pacing lead 100 having a helical fixation device 104. In this case, the lead illustrated corresponds to that disclosed in U.S. Pat. No. 3,737,579 issued to Bolduc, and incorporated herein by reference above. The lead includes an elongated insulative lead body 108 which contains therein an elongated conductor which is coupled to fixation helix 104. In this particular lead, therefore, the fixation helix 104 also serves as an electrode. Fixation helix 104 exits the lower surface of the electrode head 102 which is also molded of insulated plastic and carries around its external periphery a DACRON® fiber mesh skirt 106.

As illustrated, the tongs 22 and 24 are shown gripping the electrode head 102 and are maintained in engagement with the electrode head by means of the spring 46 internal to the handle (FIG. 4), in the manner discussed above. In order to attach the lead to the surface of the heart 110, the rotatable portion of the handle 16 (FIG. 1) is rotated while the fixation helix 104 is placed in contact with heart tissue 110. Rotation of the rotatable portion 16 of the handle causes corresponding rotation of the tongs 22 and 24, screwing the lead into heart tissue. After the lead has been screwed into heart tissue, the rotatable portion 16 of the handle (FIG. 1) is moved distally toward the stationary portion 18 of the handle, allowing tongs 22 and 24 to move distally relative to the outer shaft tubing 26 and the nose cap 20 and allowing the tongs to expand away from the electrode head 102, allowing the tool to be disengaged from the electrode head.

In conjunction with the above specification, we claim:

1. A tool for implanting a lead having a fixation helix, comprising:
   a curved, elongated shaft;
   a rotatable gripping mechanism mounted at a distal end of the shaft; and
   a handle, mounted at a proximal end of the shaft;
   means for rotating the gripping mechanism relative to the shaft; and
   means for causing the gripping mechanism to grip and release a lead.

2. A tool according to claim 1 wherein the gripping mechanism comprises a pair of tongs and wherein the means for causing the gripping mechanism to grip and release a lead comprises means for causing the tongs to move toward and away from one another.

3. A tool according to claim 2 wherein the means for causing the tongs to move toward and away from one another comprises a longitudinally movable cable extending through the shaft, coupled to the gripping mechanism and a bearing against which the tongs slide when the cable is moved longitudinally.

4. A tool according to claim 3 wherein the tongs extend distally of the bearing and angle extend radially outward of the bearing whereby when the cable is moved proximally relative to the bearing, distal portions of the tongs approach one another.

5. A tool according to claim 3 or claim 4 further comprising means for maintaining the grip of the tongs on a pacing lead, comprising means for maintaining a force pulling the cable proximally relative to the shaft.

6. A tool according to claim 5 wherein the force maintaining means comprises a spring.

7. A tool according to claim 1 or claim 2 or claim 3 or claim 4, further comprising means for maintaining the grip of the tongs on a pacing lead.

8. A tool according to claim 3 or claim 4 wherein the cable is rotatable.

9. A tool according to claim 8 wherein the rotating means comprises means for rotating the cable, mounted to the handle.

10. A tool according to claim 1 or claim 2 or claim 3 or claim 4 wherein the rotating means comprises a rotatable cable extending through the shaft, coupled to the gripping mechanism.

11. A tool according to claim 10 wherein the rotating means further comprises means for rotating the cable, mounted to the handle.

12. A tool for implanting a lead having a fixation helix, comprising:

a curved, elongated shaft;

rotatable tongs mounted at a distal end of the shaft, extending distally from the shaft and angle radially outward;

a bearing, located in a distal portion of the shaft, against which the tongs slide;

a handle, mounted at a proximal end of the shaft;

a cable, rotatable and longitudinally movable relative to the shaft, extending through the shaft and coupled to the tongs;

means for rotating the cable mechanism relative to the shaft and for moving the cable longitudinally relative to the shaft, mounted to the handle.

13. A tool according to claim 12, further comprising means for maintaining a force pulling the cable proximally relative to the shaft.

14. A tool according to claim 12 wherein the means for rotating and moving the cable comprise a rotatable and longitudinally movable member, mounted to the handle.

15. A tool according to claim 14 further comprising a spring, urging the movable member proximally relative to the shaft.

* * * * *